United States Patent [19]

Henn et al.

[11] Patent Number: 4,961,985

[45] Date of Patent: Oct. 9, 1990

[54] FABRICS FOR PROTECTIVE CLOTHING

[75] Inventors: Robert L. Henn; Dilip J. Sakhpara, both of Newark, Del.; Christian E. Bailey, Port Deposit, Md.; John J. Bowser, Newark, Del.; Peter L. Brown, Elkton, Md.

[73] Assignee: W. L. Gore & Associates, Inc., Newark, Del.

[21] Appl. No.: 215,669

[22] Filed: Jul. 6, 1988

[51] Int. Cl.$^5$ .................................................. B32B 3/00
[52] U.S. Cl. ........................... 428/196; 2/DIG. 7; 128/849; 428/246; 428/247; 428/253; 428/284; 428/286; 428/290; 428/315.9; 428/422; 428/423.1; 604/382
[58] Field of Search ............... 428/315.5, 315.7, 315.9, 428/316.6, 422, 245, 246, 252, 253, 284, 196, 286, 247, 290, 423.1; 604/382; 128/849; 2/DIG. 7

[56] References Cited

U.S. PATENT DOCUMENTS

| | | | |
|---|---|---|---|
| 3,953,566 | 4/1976 | Gore | 264/288 |
| 4,187,390 | 2/1980 | Gore | 174/102 R |
| 4,194,041 | 3/1980 | Gore et al. | 428/423.1 |
| 4,344,999 | 8/1982 | Gohlke | 428/316.6 |
| 4,433,026 | 2/1984 | Molde | 428/252 |
| 4,443,511 | 4/1984 | Worden et al. | 428/198 |
| 4,532,316 | 7/1985 | Henn | 428/423.1 |
| 4,539,255 | 9/1985 | Sato et al. | 428/315.5 |
| 4,547,423 | 10/1985 | Kojima et al. | 428/315.5 |
| 4,561,435 | 12/1985 | McKnight | 128/156 |
| 4,613,544 | 9/1986 | Burleigh | 428/315.5 |
| 4,636,424 | 1/1987 | Amemiya et al. | 428/315.5 |
| 4,692,369 | 9/1987 | Nomi | 428/422 |
| 4,818,596 | 4/1989 | Cook et al. | 428/315.9 |
| 4,833,026 | 3/1989 | Kausch | 428/315.5 |

FOREIGN PATENT DOCUMENTS

| | | |
|---|---|---|
| 0123966 | 11/1984 | European Pat. Off. . |
| 184392 | 6/1986 | European Pat. Off. . |
| 211505 A | 2/1987 | European Pat. Off. . |
| 1213283 | 11/1970 | United Kingdom . |
| 1254933 | 11/1971 | United Kingdom . |
| 1310460 | 3/1973 | United Kingdom . |
| 1339207 | 11/1973 | United Kingdom . |
| 2024100 | 1/1980 | United Kingdom . |
| 2131678 A | 6/1984 | United Kingdom . |

Primary Examiner—James J. Bell
Attorney, Agent, or Firm—Gary A. Samuels

[57] ABSTRACT

A coated product is provided that is comprised of a substrate and a coating comprised of a microporous scaffold material having a high void volume and open, interconnecting void microstructure, the scaffold material having a layer of a selected polyurethane thereon which extends in the voids. The coated product has good barrier properties with respect to bacteria, viruses, and air-borne particulate.

34 Claims, 5 Drawing Sheets

FABRICS FOR PROTECTIVE CLOTHING

FIELD OF THE INVENTION

This invention relates to a new form of coated fabrics and a method for manufacturing them. More particularly, the invention relates to such fabrics which provide barrier protection against microorganisms, such as bacteria and viruses, and against airborne particulate matter.

BACKGROUND OF THE INVENTION

Surgical gowns, drapes and the like protect surgically prepared areas of the skin from contamination and also protect surgeons and nurses against contamination through contact with unprepared or contaminated areas of patient's skin. In addition, surgical gowns should present a sterile barrier to protect patients from contamination through contact with the surgeon, and vice versa.

Liquid imperviousness of the gown or drape is recognized as an important property in assuring that the gown or drape presents a sterile surface and acts as a barrier to the passage of bacteria or virus. Body liquids and other liquids can permeate through the surgical gown or drape and contact the skin of the patient. Thus, bacteria and viruses, such as the AIDS virus, which are present on the surface of the gown or drape may be transported through the gown to the patient or the operating room personnel.

In addition to being liquid repellent and a bacteria and viral barrier, hospital gowns desirably present a non-glare outer surface, are nonlinting, possess antistatic characteristics and, not least importantly, are comfortable to wear.

It has been widely recognized that garments must be "breathable" to be comfortable. However, it is not necessary that air pass through the garment for it to be comfortable, only that water vapor from perspiration be transmitted from inside to outside so that undergarments do not become wet and so that a natural evaporative cooling effect can be achieved. Breathability and ability to transport interior moisture vapor to the external environment are used interchangeably herein. If a continuous film of hydrophilic material is exposed to air containing substantial water vapor on one side of the film, and to air containing less water vapor on the other side, the side of the film exposed to the higher water vapor concentration will absorb water molecules which diffuse through the film and are desorbed or evaporated on the side exposed to the lower water vapor concentration. Thus, water vapor is effectively transported through the film on a molecule by molecule basis. This property is known as "breathability".

One type of commonly used protective clothing is made from a polyolefin nonwoven substrate. While having reasonable properties for protection, garments constructed of this material are known to be very uncomfortable due to their inherent low moisture transmission characteristics, i.e their low breathability. Various attempts have been made to improve breathability of this nonwoven material. These efforts, however, result frequently in a more open structure of the nonwoven material and thus also simultaneously lower its protection value. Coatings on spun-bonded polyolefin have been employed to afford greater barrier protection to the 'open' base structure of the nonwoven. However, the already inherently low moisture transmission characteristics of the spun-bonded material are even further reduced, simultaneously reducing the comfort of garments made by use of this technology.

Protective clothing in hospital operating rooms has been made of wood-pulp filled, spunlaced polyester, heavily treated with a water-repellent. Here again a compromise in properties must be reached. Greater comfort sacrifices maximum microorganism barrier protection and greater barrier protection lowers comfort. For instance, where hospital operating room gown products require superior protection from microorganisms over the base spun-laced polyester, a polyethylene film is usually laminated to the polyester. But, while achieving good barrier characteristics, moisture vapor transmission is substantially eliminated.

As seen from the foregoing, protection properties and comfort properties are traded off with one another. The present invention allows for both very desirable barrier protection characteristics while simultaneously achieving good moisture vapor transmitting characteristics; i.e. protection with comfort.

SUMMARY OF THE INVENTION

A discovery has now been made in which the combination of a porous scaffold material, a hydrophilic polyurethane resin, and a substrate, all in proper relationship to one another, results in a coated product having desirable aesthetics and having useful microorganism and particulate barrier properties. Specifically, the coated product provides a functional barrier without compromising the comfort to the wearer. The functional barrier provided serves as an effective barrier to microorganisms and air-borne particulates.

In this invention, a coating is applied to one side of a substrate in a particular manner to impart the desired barrier features. The coating is a combination of both a polymeric microporous scaffold layer and a hydrophilic polyurethane resin.

Accordingly, the product of this invention is a coated fabric which comprises:

(a) a substrate fabric having a moisture vapor transmission rate of at least 5000, preferably at least 10,000, most preferably at least 15,000 gm/m$^2$/24 hr. and., (b) a coating on at least one side of said fabric comprising a polymeric porous, scaffold material having a microstructure of open interconnected voids wherein the void volume of the scaffold material is at least 65% of the total scaffold material volume, said scaffold having a weight of between 1 and 10 grams per square meter; said scaffold having a layer of hydrophilic, polyurethane resin on one surface of the scaffold, which extends into a portion of the voids of the scaffold, said polyurethane layer having a weight of between 5 and 25, preferably 10–20 gm/square meter; said coating being applied to the fabric on the side containing the resin., said article being a microorganism barrier such that it does not permit passage of viruses when challenged by the Virus Barrier Efficiency Test (VBET) at 4 psi; and said article being an airborne particulate barrier such that it exhibits an air permeability less than 6 cc per minute by the Gurley air permeability test.

The surface of the coated fabric has a pleasing appearance which is due to the fact that the polyurethane resin does not fill the voids of the scaffold to the extent that the resin is present on the opposite side of the scaffold. Alternatively, to ensure that there is an exposed microporous face on the opposite side, a second layer of untreated scaffold can be applied to that surface.

The products of this invention, are continuous coatings and as such exhibit substantially no air permeability and so afford a barrier to air-borne particulates. Furthermore, the products of this invention function as a barrier to microorganisms, such as viruses and bacteria. These barrier characteristics are achieved while the moisture vapor transmission rate (MVTR) of the coated product is only slightly lower than the MVTR of the uncoated starting substrate. Thus the product of this invention yields both protection and comfort maximizing both without compromising either. Notably, these features are also retained following gamma radiation sterilization.

A method of making the coated product is also provided which comprises combining the coating to the fabric substrate.

A method of challenging the coated product with viruses and determining the functional integrity of the coating is also provided.

DETAILED DESCRIPTION OF THE INVENTION

Figure 1:
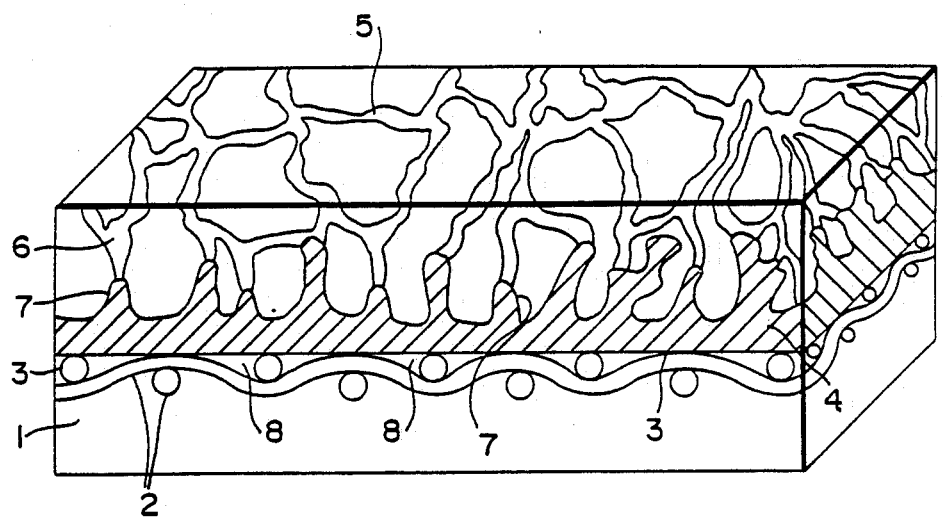
FIGS. 1 and 2 depict the construction of one embodiment of the invention.

As used herein, a coated product or fabric is one in which a substrate is covered continuously on a surface with one or more materials to give the substrate a property it does not possess by itself.

The substrate used in this invention can be any fabric that has a moisture vapor transmission rate of at least 5000 gm/m$^2$/24 hr. The fabric may be woven, nonwoven or knitted. The substrate may be made of paper. It may also have the form of a scrim, mesh, or grid. In applications such as hospital gowns, a textile fabric, such as a polyester-cotton blend, or a nonwoven material that contains wood pulp is often used as the substrate.

The polymeric scaffold material is a microporus polymer having a microstructure of open, interconnecting voids and void volume of greater than 5%. It may preferably have a void volume greater than 70% or even 85%, for some applications. The scaffold material may have a thickness of less than 100 microns, preferably less than 35 microns, and most preferably less than 20 microns.

Scaffold materials include films of microporous polyolefins, such as polytetrafluoroethylene, polypropylene, polyethylene and other microporous polymers, which possess high moisture vapor transmission rates.

A preferred scaffold material is expanded polytetrafluoroethylene (PTFE). This material is characterized by a multiplicity of open, interconnecting voids, high strength, and stable chemical properties. U.S. Pat. No. 3,953,566 and 4,187,390, describes the preparation of the desirable microporous, expanded, polytetrafluoroethylene films. These films are commercially available from W. L. Gore & Associates, Inc., and are sold under the trademark GORE-TEX.

The hydrophilic polyurethane layer selectively transports water by diffusion but does not support pressure driven liquid flow. Therefore moisture is transported, but the continuous layer precludes passage of microorganisms and air.

The polyurethanes useful herein comprise the product of a polyol of primarily oxyethylene units and a polyisocyanate. The polyol moiety comprises greater than 45% by weight of polyurethane, preferably greater than 60%, most preferably greater than 70%.

One class of such polyurethanes are those that have a backbone of polyoxyethylene which end with toluene diisocyanate groups. It has a branched polyether with at least three reactive isocyanate groups.

Another class of polyurethanes comprise the reaction product of:

(i) a polyol A having a number average molecular weight of from about 600 to about 3500 and having a functionality of at least 2;

(ii) an isocyanate (B) having a functionality of at least 2; and (iii) a low molecular weight chain extender (C) having a molecular weight in a range lower than about 500 and having a functionality of at least 2, wherein the reactants are employed in such proportions so as to satisfy the following equations:

$$\frac{EqNCO}{EqOH + EqCE} \geq 1.1$$

$$EqOH \geq EqCE$$

$$EqCE > 0,$$

wherein EqNCO is the equivalent of the isocyanate species employed, and EqOH and EqCE denote the respective molar equivalents of the polyol and chain extender employed, the soft segments being provided by the polyol of primarily oxyethylene units, and the suitable hard segments being provided by the reaction product of the isocyanate and chain extender and which induce phase-separation of the hard and soft segments.

Preferred is the reaction product of:

(i) a polyol (A) of primarily oxyethylene units, having a number average molecular weight of from about 600 to about 3500;

(ii) a polyisocyanate (B); and (iii) a low molecular weight bifunctional chain extender (C) having a molecular weight in a range lower than about 500.

Most preferred is the reaction product of:

(i) a poly(alkylene ether)glycol (A) of primarily oxyethylene units, having a number average molecular weight of from about 600 to about 3500;

(ii) a diisocyanate (B); and (iii) a low a molecular weight bifunctional chain extender (C) having a molecular weight in a range lower than about 500.

These polyurethanes are described in greater detail in U.S. Pat. No. 4,532,316.

To prepare the products of the invention, the polyurethane in the form of its liquid phase is applied to one side of the scaffold material in a controlled amount so as to form a layer on the material and to partially infiltrate the voids of the material. The substrate is combined with the polyurethane side of the polyurethane/scaffold combination (coating) and subsequently caused to solidify and/or cure in a firm bond between the substrate and the coating.

Figure 5:
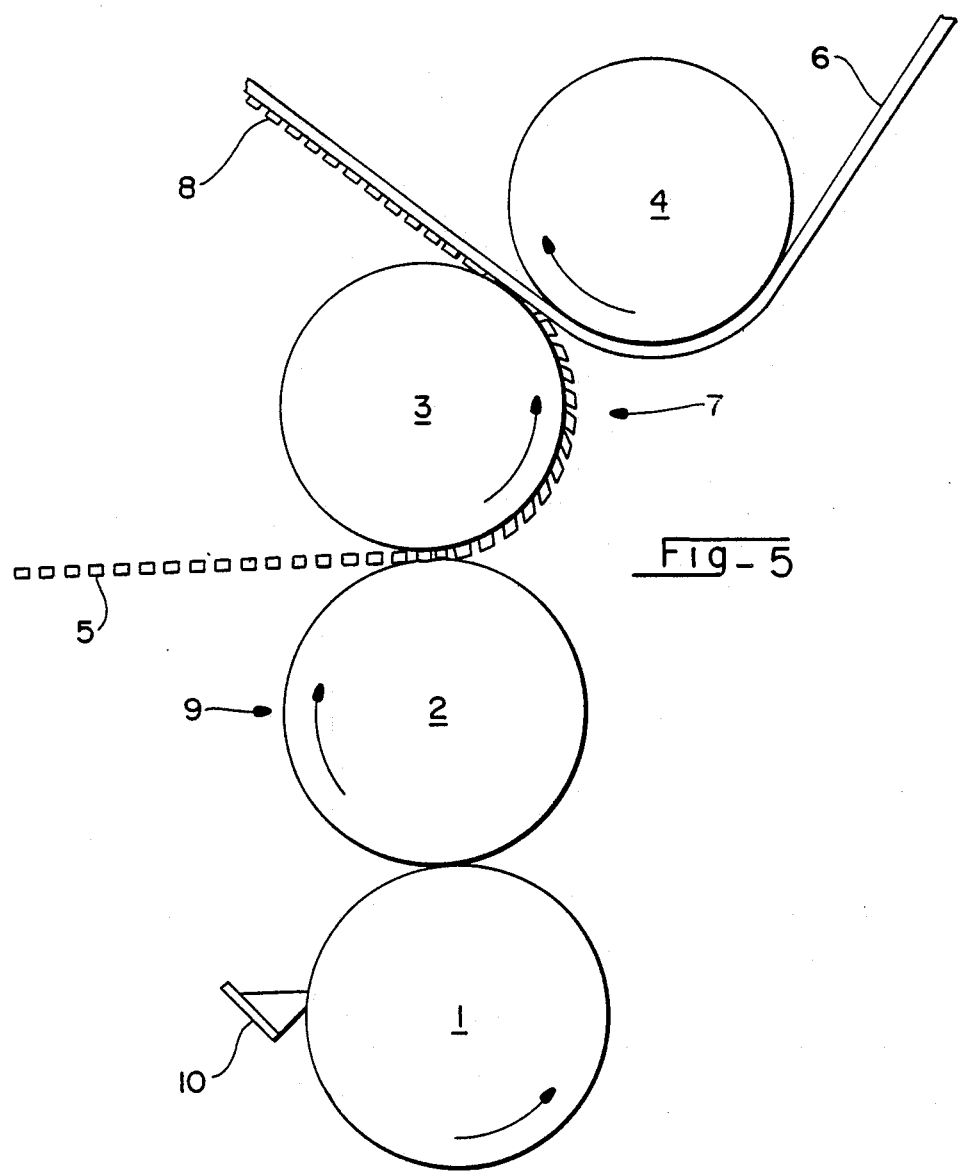
FIG. 5 is a schematic drawing of the process used in the invention.

The coating method is illustrated but not limited to the following description of a four roll stack as illustrated in FIG. 5. Metered control of polyurethane is provided for by a gravure roll, 1, and doctor blade/feed reservoir, 10. The polyurethane, 9, is applied in a controlled amount to the continuously moving, scaffold material, 5, in the nip between two rotating rolls, 2 and 3; one such rotating roll, 2, carrying a controlled amount of the polyurethane and the other such roll, 3, providing support so as to force the polyurethane partially into the porous structure of the scaffold material, 5.

The coating, 7, (i.e. the scaffold material and polyurethane combination) is combined with the substrate, 6, in the nip between two rotating rolls, 3 and 4, resulting in the coated product, 8, of this invention. This method can be further modified to allow for a second substrate to be brought into the backside of the coating to cause a sandwich effect, the coating being between the two substrates.

The pressure between rolls 2 and 3 and the amount of polyurethane flow are adjusted to result in the polyurethane both coating the scaffold material surface and infiltrating the voids of the scaffold to a predetermined extent. Care is taken, however, not to completely fill the voids of the microporous scaffold.

Figure 2:
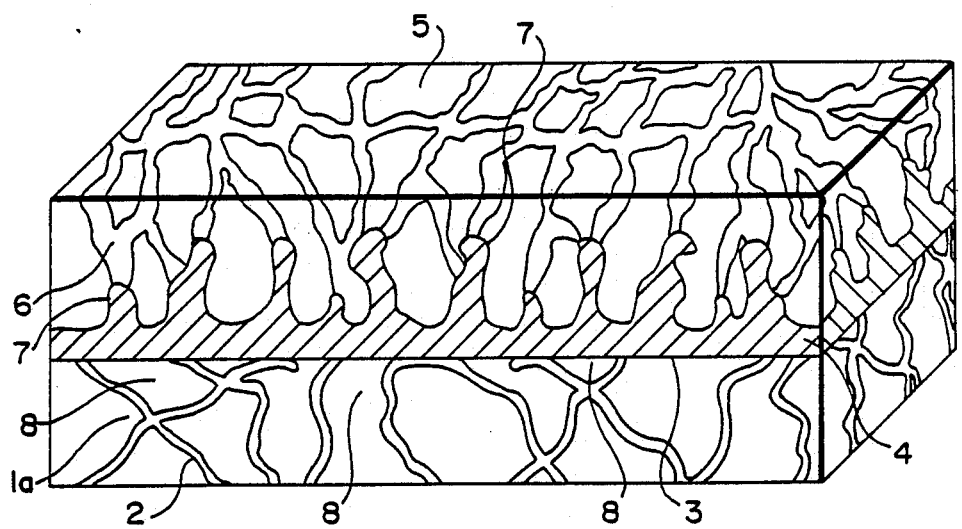

Referring to FIGS. 1 and 2, which depicts a representative coated product of this invention, substrate 1 is shown as a woven fabric made of fibers 2 in FIG. 1 and as a nonwoven fabric in FIG. 2. Raised or elevated portions of the fabric are shown as 3. The polyurethane layer is shown as 4, and as seen, contacts and adheres to the substrate at raised or elevated points 3. Airspaces in the fabric are depicted as 8. The scaffold material is shown as 5 and the voids are shown as 6 and are partially filled with polyurethane as shown at 7.

The coating, the (combination of the polyurethane and scaffold material) is attached to the substrate in an unique way. The coating and the substrate attach only at elevated specific points. This is contrasted against what is normally seen in the prior art, where coatings in general seems to follow the contour of the substrate and/or fill in the voids and valleys in the substrate and as such is seen to not have an overall regular thickness. In otherwords, the coating herein on a microscopic scale is seen to span between the points of contact of the substrate rather than follow the contours of the surface.

It is believed that it is this phenomenon that produces the good drape of the fabrics. Drape is defined as the way a fabric falls when hung in different positions. Drape is associated with flexibility and suppleness. Furthermore it is believed that it is the combination of scaffold & polyurethane that allows for such a thin hydrophilic polyurethane layer to be so continuous. It is this continuity that provides the desired functional barrier properties and the thinness that allows such high rates of water transfer.

While the products of this invention find usefulness in hospital gowns because of their good viral and bacterial barrier properties, they also find use in other applications where such good microorganism barrier properties are desirable, such as hospital bedding, incontinent devices, hygienic products, and other like applications.

The products of this invention also provide utility in applications where barrier control of airborne particulates are desired. For instance they find usefulness in asbestos clean-up where the worker needs to be comfortable, yet protected. Turning the protection concept around, the product also provides utility also in keeping body particulates away from sensitive material manufactured or used within a clean room.

In the course of testing for bacterial and virus barriers for use in operating room garments, the work of Laufman, et al (Am. Surg. 875, June 1975) was taken into account. They measured the stress forces on surgical barriers while in use and found forces in the order of 5 lbs at the elbow and 10 lb. at the waiste. Assuming the elbow area encompasses a 4 inch diameter circle and the waist an area of 36 inches, these forces equate to 0.40 psi and 0.28 psi, respectively. To provide a degree of safety, virus barrier testing was performed with pressure up to 4 psig across the membrane test specimen.

Test Procedures

A variety of different tests have been used in the Examples. These are described as follows:

Air Permeability Determination

Substrates and coated products of this invention were tested for Gurley seconds, defined as the time in seconds for 100 cc of air to flow through 6.45 cm$^2$ of test material under a pressure drop of 1.2 kPa. The Gurley seconds were converted to air permeability by dividing them into the 100 cc of air. As such the air permeability is reported in cc/min. of air through the test area. The test device, a Gurley Densometer Model 4110, or Model 4120, was employed in a method similar to Method A of ASTM D726-58. Model 4110 was used on uncoated substrates, 4120 on coated samples. Coated samples were oriented coating face up to ensure as an effective seal as possible, however care must be taken to minimize the leakage around the edge of the test area. As such an air permeability of less than 6 cc/min was used as the criteria herein to demonstrate no air flow.

Moisture Vapor Transmission Test

A description of the test employed to measure moisture vapor transmission rate (MVTR) is given below. The procedure has been found to be suitable for testing coatings and coated products.

In the procedure, approximately 70 ml of a saturated salt solution of potassium acetate and distilled water was placed into a 133 ml polypropylene cup, having an inside diameter of 6.5 cm at the mouth. An expanded PTFE membrane, having a Gurley number of about 7 seconds, a bubble point of about 179 kPa determined as described in ASTM F316, thickness of about 37 microns and a weight of about 20 gms/m$^2$, available from W. L. Gore & Associates of Newark, Del., was heat sealed to the lip of the cup to create a taut, leakproof, microporous barrier containing the salt solution. A similar expanded PTFE membrane was mounted taut within 12.5 cm embroidery hoop and floated upon the surface of a water bath. The water bath assembly was controlled at 23° C. plus or minus 0.1° C., utilizing a temperature controlled room and a water circulating bath.

Coated samples are then placed coated side down onto the surface of the floating expanded PTFE membrane.

The cup assembly weighed to the nearest 1/1000 gm and was placed in an inverted manner onto the center of the test sample.

Water transport was provided by the driving force between the water and the saturated salt solution providing water flux by diffusion in that direction. The sample was tested for 15 minutes and the cup assembly was then removed, weighed again to within 1/1000 gm.

The MVTR of the sample was calculated from the weight gain of the cup assembly and was expressed in grams of water per square meter of sample surface area per 24 hours.

A second cup assembly was simultaneously weighed to within 1/1000 gm and placed onto the test sample in an inverted manner as before. The test was repeated until a steady state MVTR was observed by two repetitive MVTR values. With thin coatings (less than 0.25 mm), this generally has been found to require only one test interval to achieve steady state information within the variability of the test.

Suter Continuity Test

Coated products of the present invention were tested for coating continuity using a modified Suter test apparatus, which is a low water entry pressure challenge. Water was forced against a sample of 10 cm diameter sealed by two rubber gaskets in a clamped arrangement. The sample was mounted with the coating side down against the water. It is important that a leakproof seal is formed by the clamp mechanism, gaskets and sample. In deformable samples, the sample was held in place by a reinforcing scrim (e.g. open nonwoven). The sample was open to atmospheric conditions and was visible to the operator. The water pressure on the sample was increased to 6.89 kPa by a pump connected to a water reservoir, as indicated by an appropriate gauge and regulated by an in-line valve. The test sample was at an angle and the water was recirculating to assure water contact and not air against the sample's lower surface. The upper surface of the sample was visually observed for a period of at least 1 minute for the appearance of any water which would be forced through the sample. Liquid water seen on the surface was interpreted as a deficiency in the continuity of the coating. A passing grade was given for no liquid water visible within 3 minutes, thus indicating a continuous coating.

Virus Barrier Efficiency Test

Figure 3A:
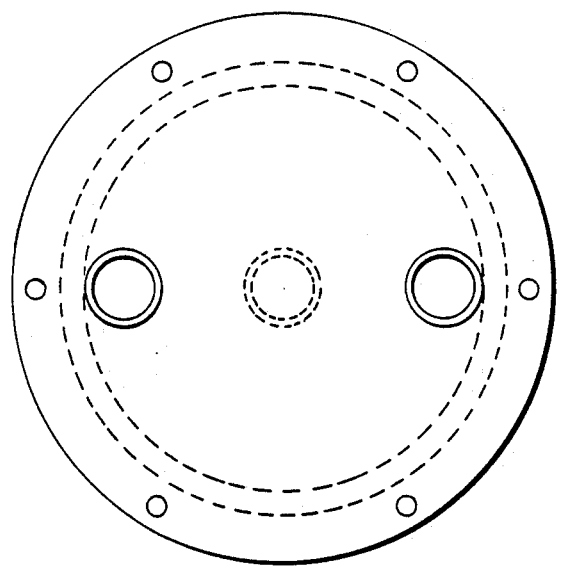
FIGS. 3 and 4 depict views of a machine used to test coated fabrics for viral barrier efficiency.
Figure 3B:
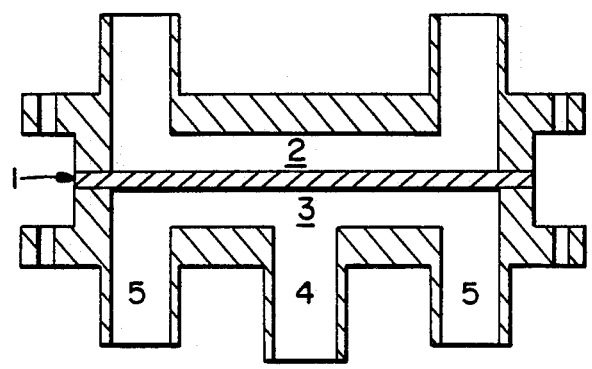
Figure 4:
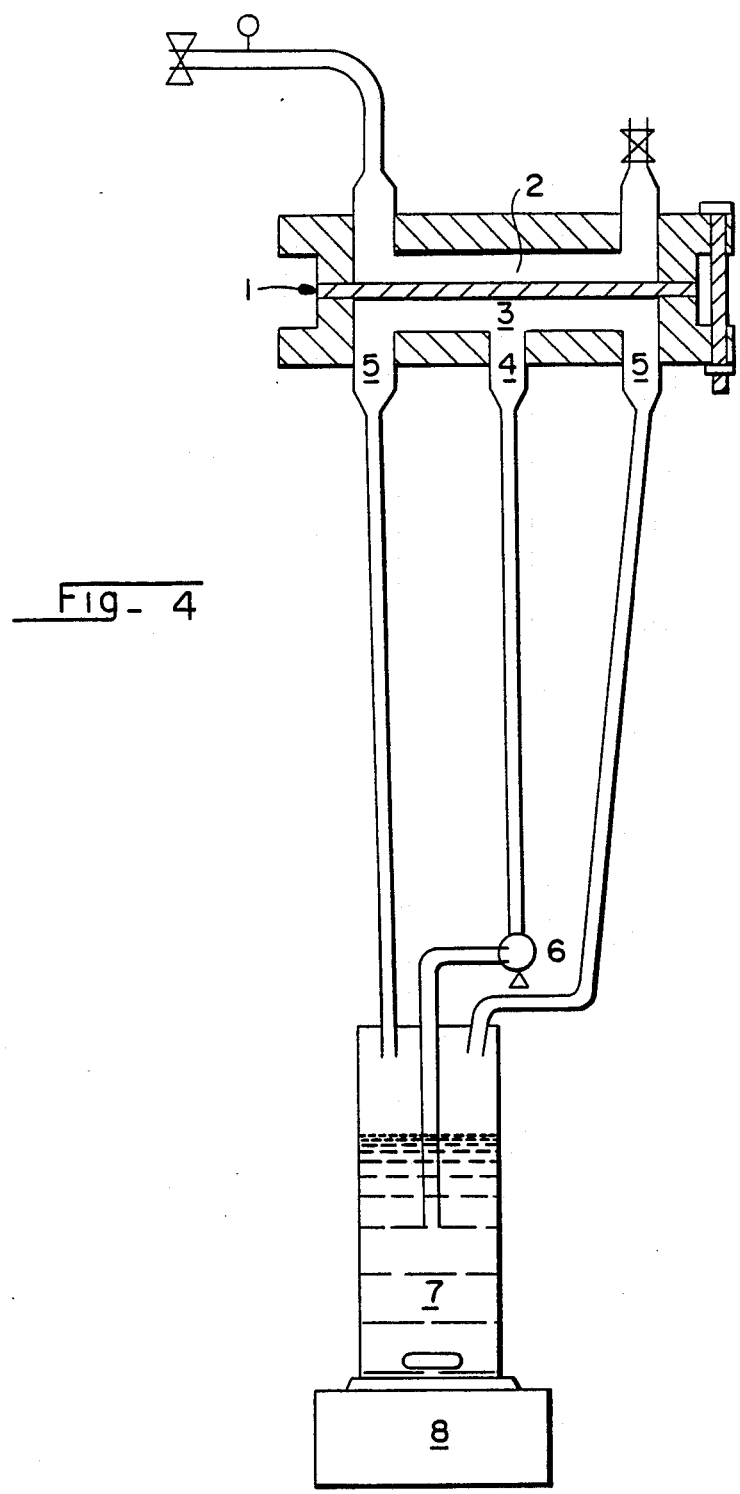

A jig, as shown in FIGS. 3 and 4 was designed to hold the barrier being challenged.

Above the barrier the virus suspension is contained in a pressurizable reservoir.

Below the barrier a second reservoir contains a tryptone broth which is pumped so the bottom of the barrier is continuously washed by the broth. The washings are returned to a holding vessel for the broth. The upper reservoir is filled with a virus suspension (at least $1 \times 10^8$ virus particles/ml) and is pressurized. Any virus particles passing through the barrier are washed into the broth. After a set period of time, the broth is sampled for assay.

For testing virus barriers, a small icosahedral shaped bacteriophage (Phi-X174) with a diameter of 27 nanometers was used. The suspending liquid was human serum. The test period was 30 minutes at 0.5-1 cm. of water pressure, 30 minutes at 4 cm water pressure, 30 minutes at 1 psig. and 30 minutes at 4 psig. applied to the virus suspension reservoir. Broth samples were collected at the beginning and then at the end of each interval.

For quantification, dilute the samples serially through 10 in tryptone broth. Add 0.5 ml. of each dilution into 2.5 ml of autoclaved top agar in sterilized test tubes, add 1 drop of host bacteria suspension to each tube, mix well and pour over the surface of bottom agar plates. Incubate at 37±2° C. for 4 to 12 hours to get plaques large enough to count but not merging. Calculate the phage titer from the plaque count and report results in PFU/ml (plaque forming units/ml).

In addition, any increase in volume of the circulating broth should be noted, indicating fluid flow from the top reservoir.

Barrier efficiency is measured by observing the pressure at which virus breakthrough occurs up to 4 psig. Any break through is judged a failure. Passing is no breakthrough at 4 psig.

The media used are shown below.

| MEDIA: | |
|---|---|
| Tryptone broth: | |
| Bacto-tryptone | 10.0 g |
| KCl | 5.0 g |
| CaCl₂ | 0.15 g |
| purified water q.s. | 1000 mL |
| adjust to pH 7.3 with 2.5 N NaOH; sterilize | |
| Top agar: | |
| Bacto-agar | 6.5 g |
| tryptone | 13.0 g |
| NaCl | 8.0 g |
| Glucose | 3.0 g |
| sodium citrate | 2.0 g |
| purified water q.s. | 1000 mL |
| Add each ingredient in order. Adjust to pH 7.5 with 2.5 N NaOH or HCl; autoclave. | |
| Bottom agar: | |
| Bacto-agar | 10.0 g |
| typtone | 13.0 g |
| NaCl | 8.0 g |
| Glucose | 1.3 g |
| sodium citrate | 2.0 g |
| purified water q.s. | 1000 mL |
| Add each ingredient in order. Adjust to pH 7.5 with 2.5 N NaOH or HCl; autoclave, pour into plates. | |

FIG. 2 is a drawing of the jig used in the virus barrier efficiency test. 1 is the barrier under test, 2 is the reservoir holding the virus suspension, 3 is the reservoir containing the detector solution, 4 is the inlet and 5 the outlets for circulating the detector solution.

FIG. 3 is a representation of the equipment used for testing the barrier properties with virus suspensions. The upper reservoir is fitter with a valve on each outlet, a pressure gauge and a means to a generate pressure on the virus suspension. Inlet (4) is connected to a peristaltic pump 6 which draws the detector solution from a supply vessel (7) and outlets (5) feed the detector liquid back into 7. The liquid is stirred and heated by a manetic stirrer/heater (8).

Bacteria Barrier Challenge Test

In considering the concepts of stress, surface tension, and liquid penetration, a test method was devised.

The test is a diffusion technique where the barrier is clamped in place between two aqueous solutions. One solution contains bacteria and the other solution is sterile. The obJect of the procedure is to determine if the bacteria can contaminate the sterile solution by penetrating the barrier.

Stress is established by raising the fluid level in the challenge half of the diffusion apparatus. The solution used should be in the surface tension range of blood and body fluids. Samples can be removed over time from the device without disturbing it or the test specimen. Different quality barriers can be distinguished by the options of increased time or pressure. All results are numerical by virtue of serial dilution plating.

The apparatus consists of two chambers whose open faces fit together. Each chamber has a top inlet for introducing media or for exerting pressure on that chamber and each has a sample tap at the bottom. The barrier to be tested is placed between the open faces of the two chambers and the faces are clamped together. The challenge media containing the bacteria is introduced into one chamber of the sterilized diffusion device while simultaneously adding the detector media to the second to prevent a premature pressure gradient.

The challenge media level is adjusted to give it a positive pressure vs. the detector media.

Samples are withdrawn over time from the detector broth. At the end of the test the total contents of the detector chamber should be drained and mixed prior to plating. Overnight incubation of the detector media can be used for very low count samples.

Samples are plated on agar with dilutions of 1, 100, 10,000 and 1,000,000. Results are recorded in CFU/ml (colony forming units/ml).

For these test, E. coli at a concentration of $2 \times 10^8$ CFU/ml in tripticase soy broth was used as the challenging suspension. Exposure times were 30 minutes at 4 inches of water hydrostatic head on the challenge media.

EXAMPLE 1

Figure 6:
FIG. 6 is a scanning electron microphotography of products of the invention.

A coated product was made in accordance with the present invention using the apparatus shown in FIG. 5. A roll coater was used in a 4-roll stack configuration in line with a take-up. The stack comprised of a gravure roll quadrangular pattern, 33 cells per centimeter, cell depth of 110 microns (33Q/110), pressure nipped to a polyurethane rubber roll, pressure nipped to a chrome roll, pressure nipped to a silicone rubber roll. The gravure roll was heated to 100° C. and the chrome to 100° C., the polyurethane rubber roll in contact was also at an elevated temperature. The gravure roll was with a trough containing a reactive hot melt, hydrophilic polyurethane prepared from 4.4'-diphenylmethane diisocyanate, polyoxyethylene of number average molecular weight of 1450, and hydroquinone di(2-hydroxyethyl)ether prepared according to the teachings of U.S. Pat. No. 4,532,316. The melt viscosity of said polyurethane was approximately 2000 cps as measured on a rheometer using parallel oscillating discs at the application temperature of 100° C. The hydrophilic polyurethane transferred from the gravure roll along the stack until it came in contact with the scaffold material. The scaffold material was expanded PTFE prepared according to the teachings of U.S. Pat. No. 3,953,566 and 4,187,390, having a weight of about 2–3 gm/m² and having a void volume greater than 65%. The coating (i.e. combination of scaffold and polyurethane) was brought into contact with a 70 gm/m² pulp filled polyester spunlaced nonwoven at the chrome roll/silicone roll nip. The coated product thus made was then collected on the take-up. The coated product was then cured under ambient conditions for 48 hours. The product was aesthetically pleasing having good drape. A representative photomicrograph is seen in FIG. 6 at 200x. A commercially available O.R. gown; American Converter's OPTIMA ® fabric, is representative of pulp filled polyester supnlaced nonwoven to be compared against the coated product of this invention. The final properties of the coated product are listed in Table 1 along with the OPTIMA ® substrate. All properties were characterized by the appropriate tests described above. The virus barrier efficiency test was carried out after 2.5 to 5 megarad gamma radiation sterilization.

As can be seen from the data, a high moisture transmitting product exhibiting the barrier properties claimed herein was demonstrated.

EXAMPLE 1

TABLE 1

|  | Optima Substrate | Coated Product |
| --- | --- | --- |
| Coating Weight (gm/m²) | N/A | 11.8 |
| MVTR (gms/m²/24 hrs.) | 26,700 | 22,400 |
| Suter Continuity Test (1 psig/3 min) | Fail | Pass |
| Air Permeability (cc/min.) | >6000 | <6 |
| Virus Barrier Efficiency Test (psig) | Fail (0.5–1 psig) | Pass (4 psig) |

EXAMPLE 2

To illustrate the utility of this invention the coated product described in Example 1, is compared in Table 2 to structures currently sold into the protective garment industry.

The following are representative of the materials being sold for disposable applications.

Sample 1 = spunbonded polyolefin
Sample 2 = two layers, spunbonded polypropylene
Sample 3 = spunlaced wood pulp polyester
Sample 4 = spunlaced wood pulp polyester with polyethylene film reinforcement.

In addition, Sample 5 is a high count (280), 50/50 polyester/cotton blend, fluid repellent treated, which is representative of a reuseable product was tested. All materials were tested as received.

TABLE 2

|  | Sample 1 | Sample 2 | Sample 3 | Sample 4 | Sample 5 | Coated Product of Example 1 |
| --- | --- | --- | --- | --- | --- | --- |
| Weight (gm/m²) | 47 | 112 | 76 | 123 | 217 | 85 |
| MVTR (gm/m²/24 hr.) | 5,000 | 7,400 | 26,700 | 400 | 16,500 | 22,400 |
| Suter Continuity (psig/3 min) | Fail | Fail | Fail | Pass | Fail | Pass |
| Air Permeability (cc/min.) | >6,000 | >6,000 | >6,000 | <6 | 2,140 | <6 |
| Viral Barrier Efficiency Test | NT | NT | Fail (0.5 psig) | Pass (4 psig) | Fail (0 psig) | Pass (4 psig) |

TABLE 2-continued

|  | Sample 1 | Sample 2 | Sample 3 | Sample 4 | Sample 5 | Coated Product of Example 1 |
|---|---|---|---|---|---|---|
| (psig.) |  |  |  |  |  |  |

NT = not tested as sample failed Suter continuity test.

As can be clearly seen, the product of this invention provides equal to or superior protection to all of the alternative materials and furthermore does so simultaneously with an MVTR essentially equal to or greater than the alternatives.

EXAMPLE 3

To illustrate the flexibility of this product to substrate selection, various base substrates were produced as in Example 1. Substrates illustrated:
Sample 1=67 gm/m² spunlaced 100% polyester
Sample 2=40 gm/m² spunlaced 100% polyester
Sample 3=67 gm/m² point bonded nylon
Sample 4=42 gm/m² tricot knit
The data is summarized in Table 3.

TABLE 3

|  | Sample 1 | | Sample 2 | | Sample 3 | | Sample 4 | |
|---|---|---|---|---|---|---|---|---|
|  | Control* | Coated | Control* | Coated | Control* | Coated | Control* | Coated |
| MVTR (gm/m²/24 hr.) | 25,500 | 26,200 | 31,300 | 27,700 | 27,800 | 19,600 | 46,336 | 22,300 |
| Suter Continuity Test (psig/3 min.) | Fail | Pass | Fail | Pass | Fail | Pass | Fail | Pass |
| Air Permeability Test psig (cc/min) | >6,000 | <6 | >6,000 | <6 | >6000 | <6 | >6,000 | <6 |

*The controls are the uncoated equivalent or a representative of same.

The resultant rate of moisture transfer by the product of this invention is exceptionally high. In many cases, the MVTR of the coated material is comparable to the uncoated substrate and in addition provides functional barrier properties not present in the substrate alone. To take advantage of this feature of the invention, substrates are selected with MVTR's of at least 5000 gm/m²/24 hrs. so that the substrate does not limit the high rate of moisture transfer.

EXAMPLE 4

To illustrate a most preferred range of scaffold weight, three products of this invention were made as in Example 1 with the only difference being the scaffold weight employed.

TABLE 4

|  | Coated Product A | Coated Product B | Coated Product C |
|---|---|---|---|
| Scaffold Weight (gm/m²) | 9.6 | 6.1 | 2.8 |
| MVTR (gm/m² · 24 hrs.) | 19,000 | 21,000 | 22,400 |
| Suter Continuity Test (1 psig/3 min) | Pass | Pass | Pass |
| Air Permeability (cc/min) | <6 | <6 | <6 |

EXAMPLE 5

The product of this invention can provide for the microporous face on the coating by one of two ways. Not fully penetrating the scaffold material is illustrated in Example 1. The alternative is to bring in a microporous layer as a second substrate and nip it into the coating layer of a fully penetrated scaffold layer. This nipping operation is performed immediately downstream of the 4 roll stack illustrated in FIG. 5. Table 5 compares the product of Example 1 with the product of Example 5.

TABLE 5

|  | Example 1 | Example 2 |
|---|---|---|
| MVTR (gm/m²/24 hrs.) | 22,400 | 22,500 |
| Suter Continuity Test (psig/3 min) | Pass | Pass |
| Air Permeability Test (cc/min) | <6 | <6 |
| Virus Barrier Efficiency Test (psig) | Pass (>4 psig) | Pass (>4 psig) |

EXAMPLE 6

To illustrate that a functional barrier to microorganisms includes bacterial barrier characteristics, a sample of Example 5 was tested by the bacteria barrier challenge test. The barrier proved functional by having no detectable colony formations in any of the serial dilutions of the detector fluid.

We claim:
1. A coated fabric consisting essentially of:
   (a) a substrate fabric having a moisture vapor transmission rate of at least 5000 gm/m²/24 hrs; and;
   (b) a continuous coating on at least one side of said fabric comprising a polymeric, porous, scaffold material having a microstructure of open interconnected voids wherein the void volume of the scaffold material is at least 65% of the total scaffold material volume,
   said scaffold having a weight of between 1 and 10 grams per square meter;
   said scaffold having a layer of hydrophilic, polyurethane resin on one surface of the scaffold, which extends into a portion of the voids of the scaffold;
   said polyurethane layer having a weight of between 5 and 25 gm square meters;
   said article being a microorganism barrier such that it does not permit passage of viruses when challenged by the Virus Barrier Efficiency Test at 4 psig; and said article being an airborne particulate barrier such that is exhibits an air permeability less than 6 cc per minute;
   said fabric and coating arranged so that the polyurethane resin on the coating is adjacent the fabric.
2. The coated fabric of claim 1 wherein the coating and the substrate are attached only at specific elevated points on the substrate.
3. The article of claim 1 in which the scaffold has a void volume of greater than 70%.

4. The article of claim 1 in which the scaffold has a void volume of greater than 85%.

5. The article of claim 1 in which the scaffold material has a thickness of less than 100 microns.

6. The article of claim 2 in which the scaffold material has a thickness of less than 100 microns.

7. The article of claim 3 in which the scaffold material has a thickness of less than 100 microns.

8. The article of claim 4 in which the scaffold material has a thickness of less than 100 microns.

9. The article of claim 1 in which the scaffold material has a thickness of less than 35 microns.

10. The article of claim 2 in which the scaffold material has a thickness of less than 35 microns.

11. The article of claim 3 in which the scaffold material has a thickness of less than 35 microns.

12. The article of claim 4 in which the scaffold material has a thickness of less than 35 microns.

13. The article of claim 1 in which the scaffold material has a thickness of less than 20 microns.

14. The article of claim 2 in which the scaffold material has a thickness of less than 20 microns.

15. The article of claim 3 in which the scaffold material has a thickness of less than 20 microns.

16. The article of claim 4 in which the scaffold material has a thickness of less than 20 microns.

17. The article of claim 1, 2, 3, 4 or 5, in which the scaffold material is expanded PTFE.

18. The article of claim 1 in which the scaffold is polypropylene.

19. The article of claim 1 in which the scaffold is polyethylene.

20. The article of claim 1 in which the scaffold is selected from the group: polyamide, polycarbonate, poly(ethylene terephthalate), polyester, polyacrylate, polystyrene, polysulphone, and polyurethane.

21. The article of claim 1 in which the fabric is a non-woven fabric.

22. The article of claim 1 in which the fabric is a woven fabric.

23. The article of claim 1 in which the substrate is paper.

24. The use of the article of claim 1 in a waterproof-breathable garment.

25. The use of the article of claim 1, 2, 3, 4, or 5 in a surgical gown.

26. The use of the article of claim 17 in a surgical gown.

27. The use of the article of claim 1 in a medical device.

28. The use of the article of claim 1 in packaging materials.

29. The use of the article of claim 1 as a diaper.

30. The use of the article of claim 1 as a feminine hygiene product.

31. A coated fabric of claim 1, in sterilized form.

32. The coated fabric of claim 31 in in garment form.

33. A coated fabric of claim 17 in sterilized form.

34. The coated fabric of claim 33 in garment form.

* * * * *

UNITED STATES PATENT AND TRADEMARK OFFICE
CERTIFICATE OF CORRECTION

PATENT NO. : USP 4,961,985

DATED : October 9, 1990

INVENTOR(S) : Robert L. Henn, et al.

It is certified that error appears in the above-identified patent and that said Letters Patent is hereby corrected as shown below:

Column 12, line 56, change "article" to: -coated fabric-.
Columns 12,13,14;
In each of Claims 3 through 30, change "article" in line 1 of each claim, to -coated fabric-.

Signed and Sealed this

Ninth Day of February, 1993

Attest:

STEPHEN G. KUNIN

Attesting Officer

Acting Commissioner of Patents and Trademarks